US008486706B2

(12) United States Patent
Hess et al.

(10) Patent No.: US 8,486,706 B2
(45) Date of Patent: Jul. 16, 2013

(54) L-FABP, NATRIURETIC PEPTIDES, AND CARDIAC TROPONINS IN SUBJECTS IN NEED OF CARDIAC THERAPY

(75) Inventors: Georg Hess, Mainz (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/944,785

(22) Filed: Nov. 12, 2010

(65) Prior Publication Data

US 2011/0059539 A1    Mar. 10, 2011

Related U.S. Application Data

(63) Continuation of application No. PCT/EP2009/056128, filed on May 20, 2009.

(30) Foreign Application Priority Data

May 21, 2008   (EP) .................................... 08156677

(51) Int. Cl.
*G01N 33/68*    (2006.01)
(52) U.S. Cl.
USPC .............................. 436/94; 435/6.11; 600/300
(58) Field of Classification Search
USPC ............... 436/501, 63, 94; 435/6.11; 600/300
See application file for complete search history.

(56) References Cited

U.S. PATENT DOCUMENTS

| 5,744,305 A | 4/1998 | Fodor et al. |
| 2007/0092911 A1 | 4/2007 | Buechler et al. |

FOREIGN PATENT DOCUMENTS

| EP | 0648228 B1 | 4/1995 |
| EP | 1890154 A1 | 2/2008 |
| JP | 2007-202512 A | 8/2007 |
| WO | 02/083913 A1 | 10/2002 |
| WO | 02/089657 A2 | 11/2002 |
| WO | 2005/060652 A3 | 7/2005 |

OTHER PUBLICATIONS

Ishii, Junnichi et al. "Prognostic value of combination of cardiac troponin T and B-type natriuretic peptide after initiation of treatment in patients with chronic heart failure." Clinical Chemistry (2003) 49 p. 2020-2026.*
MacDowall, P. et al. "Risk of morbidity from renovascular disease in elderly patients with congestive heart failure." The Lancet (1998) 352 p. 13-16.*
Thurman, J. M. et al. "Peeking into the black box: New biomarkers for acute kidney injury." Kidney International (Feb. 2008) 73 379-381.*
International Search Report issued Nov. 11, 2009 in PCT Application No. PCT/EP2009/056128.

International Preliminary Report on Patentability issued Jun. 16, 2010 in PCT Application No. PCT/EP2009/056128.
Abuelo, J. Gary, Normotensive Ischemic Acute Renal Failure, The New England Journal of Medicine, Aug. 23, 2007, pp. 797-805, vol. 357.
Anderson, Page A. W. et al., Molecular Basis of Human Cardiac Troponin T Isoforms Expressed in the Developing, Adult, and Failing Heart, Circulation Research, 1995, pp. 681-686, vol. 76, No. 4.
Bonow, Robert O., New Insights Into the Cardiac Natriuretic Peptides, Circulation, 1996, pp. 1946-1950, vol. 93.
Chan, Lawrence et al., Human Liver Fatty Acid Binding Protein cDNA and Amino Acid Sequence, The Journal of Biological Chemistry, Mar. 10, 1985, pp. 2629-2632, vol. 260, No. 5.
Ferrieres, Gaelle et al., Human cardiac troponin I: precise identification of antigenic epitopes and prediction of secondary structure, Clinical Chemistry, 1998, pp. 487-493, vol. 44, No. 3.
Kamijo, Atsuko et al., Urinary liver-type fatty acid binding protein as a useful biomarker in chronic kidney disease, Molecular and Cellular Biochemistry, 2006, pp. 175-182, vol. 284.
Kamijo-Ikemori, Atsuko et al., Urinary fatty acid binding protein in renal disease, Clinica Chimica Acta, Dec. 1, 2006, pp. 1-7, vol. 374, No. 1-2.
Karl, J. et al., Development of a novel, N-Terminal-proBNP (NT-proBNP) assay with a low detection limit, Scandianvian Journal of Clinical Laboratory Investigation, 1999, pp. 177-181, vol. 59, Supplement 230.
Lameire, Norbert et al., Acute renal failure, Lancet, Jan. 29, 2005, pp. 417-430, vol. 365.
Levey, Andrew S. et al., A More Accurate Method to Estimate Glomerular Filtration Rate from Serum Creatinine: A New Prediction Equation, Annals of Internal Medicine, Mar. 16, 1999, pp. 461-470, vol. 130, No. 6.
Mueller, Thomas et al., Long-term stability of endogenous B-type natriuretic peptide (BNP) and amino terminal proBNP (NT-proBNP) in frozen plasma samples, Clinical Chemistry and Laboratory Medicine, 2004, pp. 942-944, vol. 42, No. 8.
Nakamura, Tsukasa et al., Urinary Excretion of Liver-Type Fatty Acid-Binding Protein in Contrast Medium-Induced Nephropathy, American Journal of Kidney Diseases, Mar. 2006, pp. 439-444, vol. 47, No. 3.
Nakamura, Tsukasa et al., Azelnidipine Reduces Urinary Protein Excretion and Urinary Liver-Type Fatty Acid Binding Protein in Patients with Hypertensive Chronic Kidney Disease, The American Journal of Medical Sciences, 2007, pp. 321-326, vol. 333, No. 6.

(Continued)

*Primary Examiner* — Yelena G Gakh
*Assistant Examiner* — Christopher A Hixson
(74) *Attorney, Agent, or Firm* — Dinsmore & Shohl LLP

(57) ABSTRACT

Disclosed is a method for identifying a subject being susceptible to a cardiac therapy, comprising (a) determining the amounts of liver fatty acid binding protein, and at least one further polypeptide from the group of a cardiac troponin and a natriuretic peptide in at least one sample of a subject suffering from heart failure, (b) comparing the thus determined amounts to suitable reference amounts, and (c) identifying a subject being susceptible to a cardiac therapy. Also described is a device and a kit adapted to carry out the method of the present invention. Also described is the use of liver fatty acid binding protein and at least one further polypeptide from the group of a cardiac troponin and a natriuretic peptide for identifying a subject being susceptible to a cardiac therapy.

10 Claims, 3 Drawing Sheets

OTHER PUBLICATIONS

Nakamura, Tsukasa et al., Beneficial Effects of Olmesartan and Temocapril on Urinary Liver-Type Fatty Acid-Binding Protein Levels in Normotensive Patients With Immunoglobin A Nephropathy, American Journal of Hypertension, 2007, pp. 1195-1201, vol. 20.

Needleman, Saul B. and Wunsch, Christian D., A General Method Applicable to the Search for Similarities in the Amino Acid Sequence of Two Proteins, Journal of Molecular Biology, 1970, pp. 443-453, vol. 48.

Nolan, John P. and Sklar, Larry A., Suspension array technology: evolution of the flat-array paradigm, Trends in Biotechnology, Jan. 2002, pp. 9-12, vol. 20, No. 1.

Pearson, William R. and Lipman, David J., Improved tools for biological sequence comparison, Proceedings of the National Academy of Sciences, Apr. 1988, pp. 2444-2448, vol. 85.

Smith, M. W. et al., Delayed metabolism of human brain natriuretic peptide reflects resistance to neutral endopeptidase, Journal of Endocrinology, 2000, pp. 239-246, vol. 167.

Smith, Temple F. and Waterman, Michael S., Comparison of Biosequences, Advances in Applied Mathematics, 1981, pp. 482-489, vol. 2.

Warner, Timothy D. et al., Nonsteroid drug selectivities for cyclo-oxygenase-1 rather than cyclo-oxygenase-2 are associated with human gastrointestinal toxicity: A full in vitro analysis, Proceedings of the National Academy of Sciences, Jun. 1999, pp. 7563-7568, vol. 96.

Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, Vol. 50, No. 5.

Yeo, Kiang-Teck J. et al., Multicenter evaluation of the Roche NT-proBNP assay and comparison to the Biosite Triage BNP assay, Clinica Chimica Acta, 2003, pp. 107-115, Vol. 338.

Bristow, Michael R. et al., "Drugs in the Treatment of Heart Failure," Braunwald's Heart Disease, A Textbook of Cardiovascular Medicine, 7th Edition, 2005, pp. 569-601, Chapter 23, Elsevier Saunders, Philadelphia, PA.

Konkle, Barbara A. and Schafer, Andrew I., "Hemostasis, Thrombosis, Fibrinolysis, and Cardiovascular Disease," Braunwald's Heart Disease, A Textbook of Cardiovascular Medicine, 7th Edition, 2005, pp. 2067-2092, Chapter 80, Elsevier Saunders, Philadelphia, PA.

* cited by examiner

L-FABP, NATRIURETIC PEPTIDES, AND CARDIAC TROPONINS IN SUBJECTS IN NEED OF CARDIAC THERAPY

RELATED APPLICATIONS

This application is a continuation of PCT/EP2009/056128 filed May 20, 2009 and claims priority to EP 08156677.0 filed May 21, 2008.

FIELD OF THE INVENTION

The present invention relates to a method for identifying a subject being susceptible to a cardiac therapy, comprising (a) determining the amounts of liver fatty acid binding protein, and at least one further polypeptide from the group of a cardiac troponin and a natriuretic peptide in at least one sample of a subject suffering from heart failure, (b) comparing the thus determined amounts to suitable reference amounts, and (c) identifying a subject being susceptible to a cardiac therapy. Moreover, the present invention relates to a device and a kit adapted to carry out the method of the present invention. Also encompassed by the present invention is the use of liver fatty acid binding protein and at least one further polypeptide from the group of a cardiac troponin and a natriuretic peptide for identifying a subject being susceptible to a cardiac therapy.

BACKGROUND OF THE INVENTION

An aim of modern medicine is to provide personalized or individualized treatment regimens. Those are treatment regimens which take into account a patient's individual needs or risks. Personalized or individual treatment regimens shall be even taken into account for measures where it is required to decide on potential treatment regimens.

Heart failure is a condition that can result from any structural or functional cardiac disorder that impairs the ability of the heart to fill with or pump a sufficient amount of blood throughout the body. Even with the best therapy, heart failure is associated with an annual mortality of about 10%. Therefore, heart failure patients require close medical management in order to ameliorate their condition or to prevent the progression of their condition and to reduce morbidity and mortality. The medical management of heart failure patients includes the administration of drugs as well as diagnostic interventions such as coronary angiography.

Improvements during the last decades in heart failure therapy contributed to a larger life expectancy of patients suffering from heart failure. E.g., the survival of patients with heart failure can be increased by administration of angiotensin-converting enzyme (ACE) blockers, beta blockers, angiotensin receptor blockers and spironolactone. However, the administration of certain pharmaceuticals for the treatment of heart failure and for the treatment of comorbidities of heart failure may impair renal function. Therefore, heart failure patients receiving treatment should be regularly monitored for their renal function and treatment should be adjusted accordingly.

ACE inhibitors are frequently used for the treatment of heart failure since they have been clinically shown to be superior to other classes of drugs regarding the reduction of mortality.

In general, ACE inhibitors are renoprotective. However, acute rises in serum creatinine levels are observed in up to 30 percent of patient with first two months of therapy. It is known that renal impairment is a significant adverse effect of ACE inhibitors since some patients taking ACE inhibitor suffer from acute renal failure (Abuelo. N Engl J Med 2007; 357: 797-805; Lameire et al., Lancet 2005; 365: 417-30). These adverse side effects are linked to the effect of ACE inhibitors on angiotensin II-mediated functions such as renal blood flow which is affected by angiotensin II because angiotensin II vasoconstricts the efferent arterioles of the glomeruli of the kidney, and thereby increases glomerular filtration rate (GFR), a marker for renal function.

In addition to ACE inhibitors there are further drugs against heart failure which may affect renal function, particularly, NSAIDs, diuretics and antihypertensive drugs. These drugs may also result in an acute increase of serum creatinine concentration due to renal ischemia. Therefore, Abuele (loc. cit.) recommends to closely monitor patients taking these drugs, or even to stop the therapy. Stopping the therapy may be beneficial for renal function, but may worsen the condition of the patient with respect to the heart.

The effect on renal function may even be increased when concomitantly taking other pharmaceuticals such as ACE inhibitors and non-steroidal anti-inflammatory drugs.

Renal function can be assessed by determining the glomerular filtration rate (GFR). However, the determination of the GFR is very difficult, time- and cost-intensive. Therefore, renal function is typically assessed by determining the serum creatinine concentration or by assessing changes in the serum creatinine concentration. The use of creatinine as a marker for renal function, however, has been recently put into jeopardy as the serum creatinine concentration is not necessarily an accurate reflection of true renal function because the concentration also depends on other factors like age and gender. Moreover, an increase of serum creatinine levels is frequently observed only after a marked damage to functioning nephrons. Therefore, this test is not suitable for detecting early stages of renal impairment.

Thus, adverse side effects can accompany the benefits in patients with heart failure taking medication against heart failure. Therefore, it is necessary to balance the benefits of a heart failure related therapy against adverse side effects on renal function that may be caused by the therapy. Particularly, there is a need for assessing both renal function and heart function in patients with heart failure in order to adjust the dosage regimen of certain pharmaceuticals used for the treatment of heart failure.

However, although highly desirable, means and methods allowing for a reliable and efficient identification of subjects being susceptible to a cardiac therapy are not yet available.

The technical problem underlying the present invention can be seen as the provision of means and methods for complying with the aforementioned needs. The technical problem is solved by the embodiments characterized in the claims and herein below.

SUMMARY OF THE INVENTION

Therefore, the present invention relates to a method for identifying a subject being susceptible to a cardiac therapy, the subject suffering from heart failure and being in need of a cardiac therapy, comprising the steps of a) determining the amounts of liver fatty acid binding protein (L-FABP), and at least one further polypeptide from the group of a cardiac troponin and a natriuretic peptide, in at least one sample of the subject, b) comparing the amounts of the liver fatty acid binding protein, and of the at least one further polypeptide as determined in step a) to suitable reference amounts, and c) identifying a subject being susceptible to a cardiac therapy.

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification of the subject. The method may be carried out manually or assisted by automation. Preferably, step (a), (b) and/or (c) may in total or in part be assisted by automation, e.g., by a suitable robotic and sensory equipment for the determination in step (a) or a computer-implemented calculation in step (b).

DETAILED DESCRIPTION OF THE INVENTION

Figure 1:
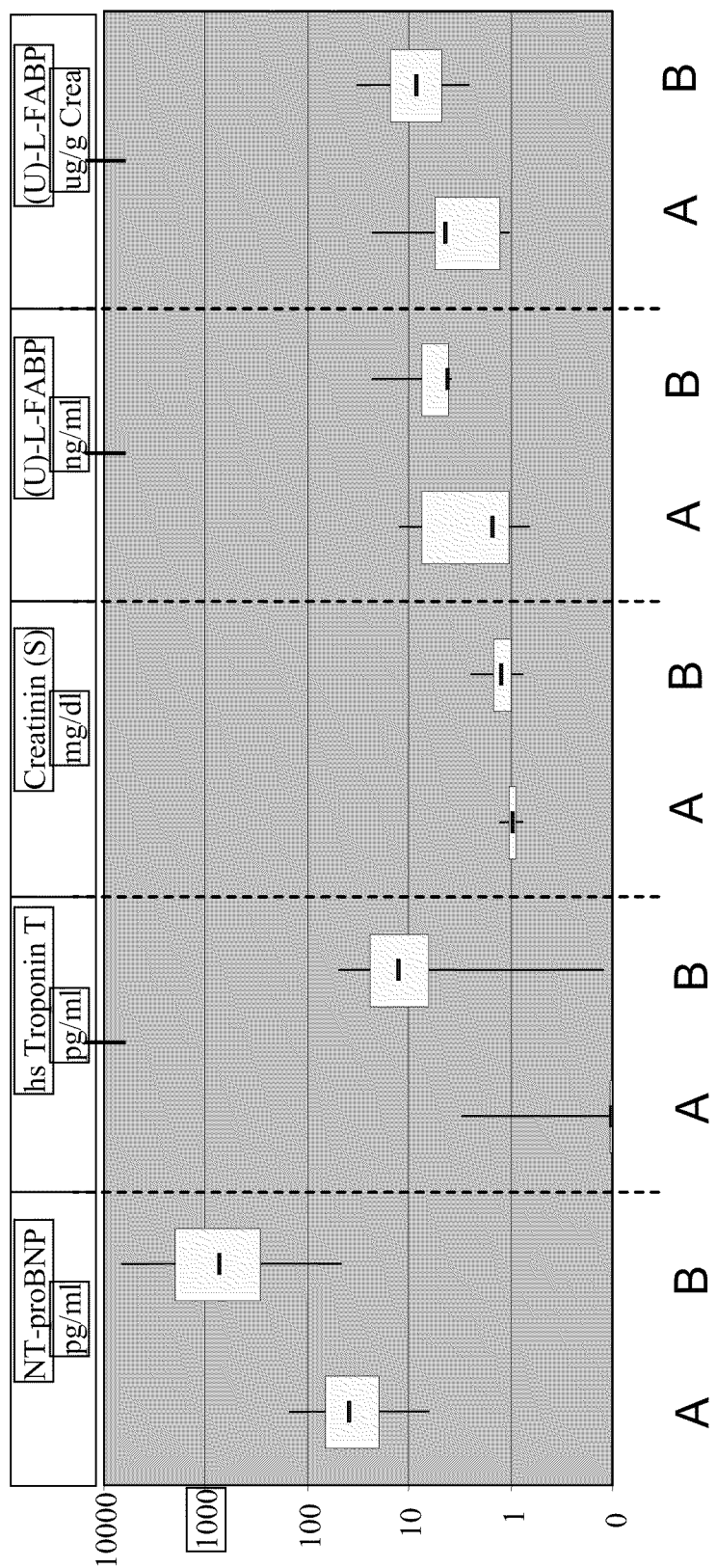
FIG. 1: Box plot analysis: Comparison of NT-proBNP, high sensitive troponin T, creatinine and urinary L-FABP in patients with heart failure and healthy individuals. The amounts of urinary L-FABP and creatinine were determined in urine samples, and the amounts of NT-proBNP and troponin T were determined in serum samples (A: healthy individuals; B: individuals with heart failure).
Figure 2:
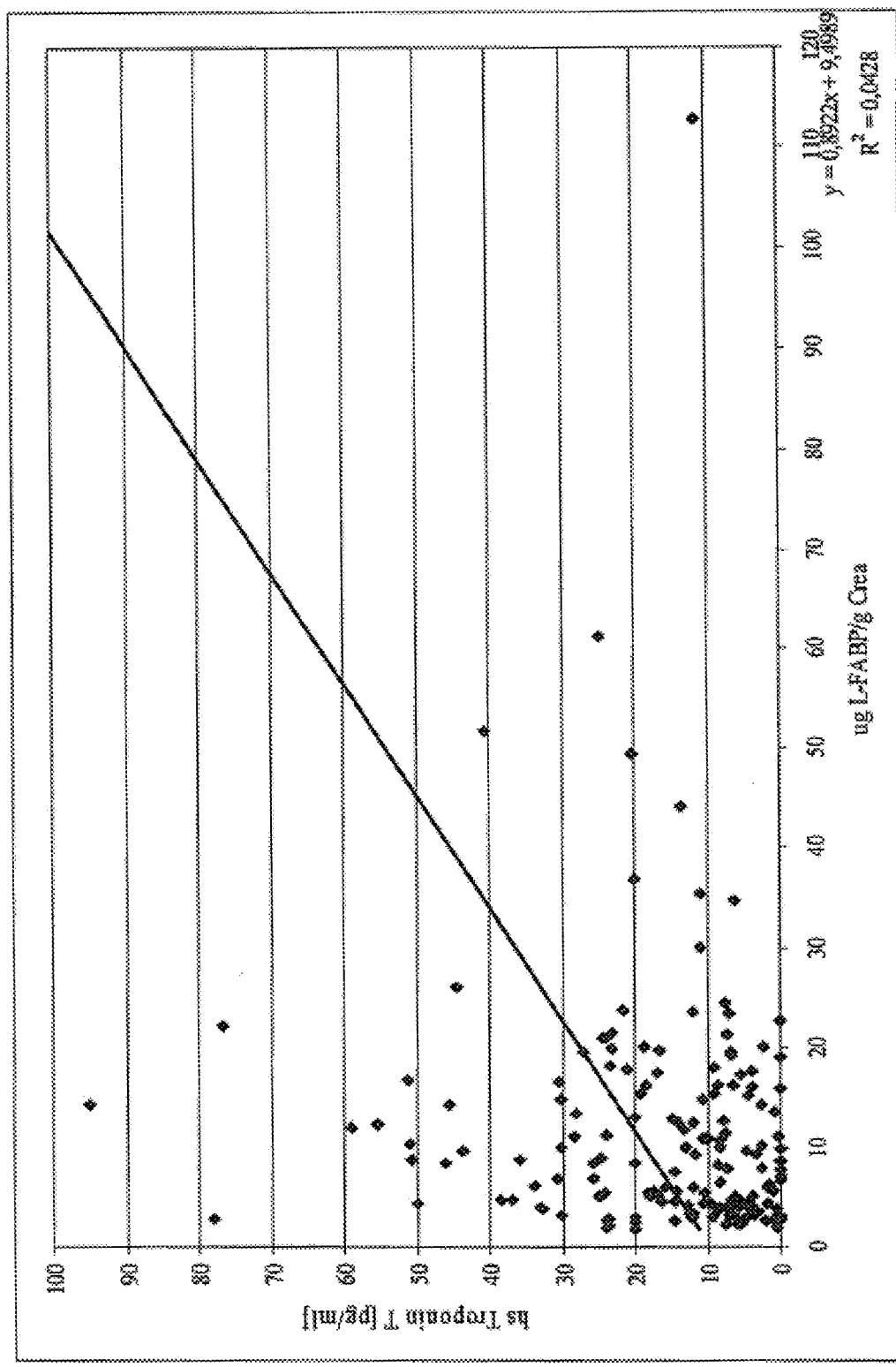
FIG. 2: Correlation of troponin T and L-FABP (L-FABP to creatinine ratio; each dot represents one individual).
Figure 3:
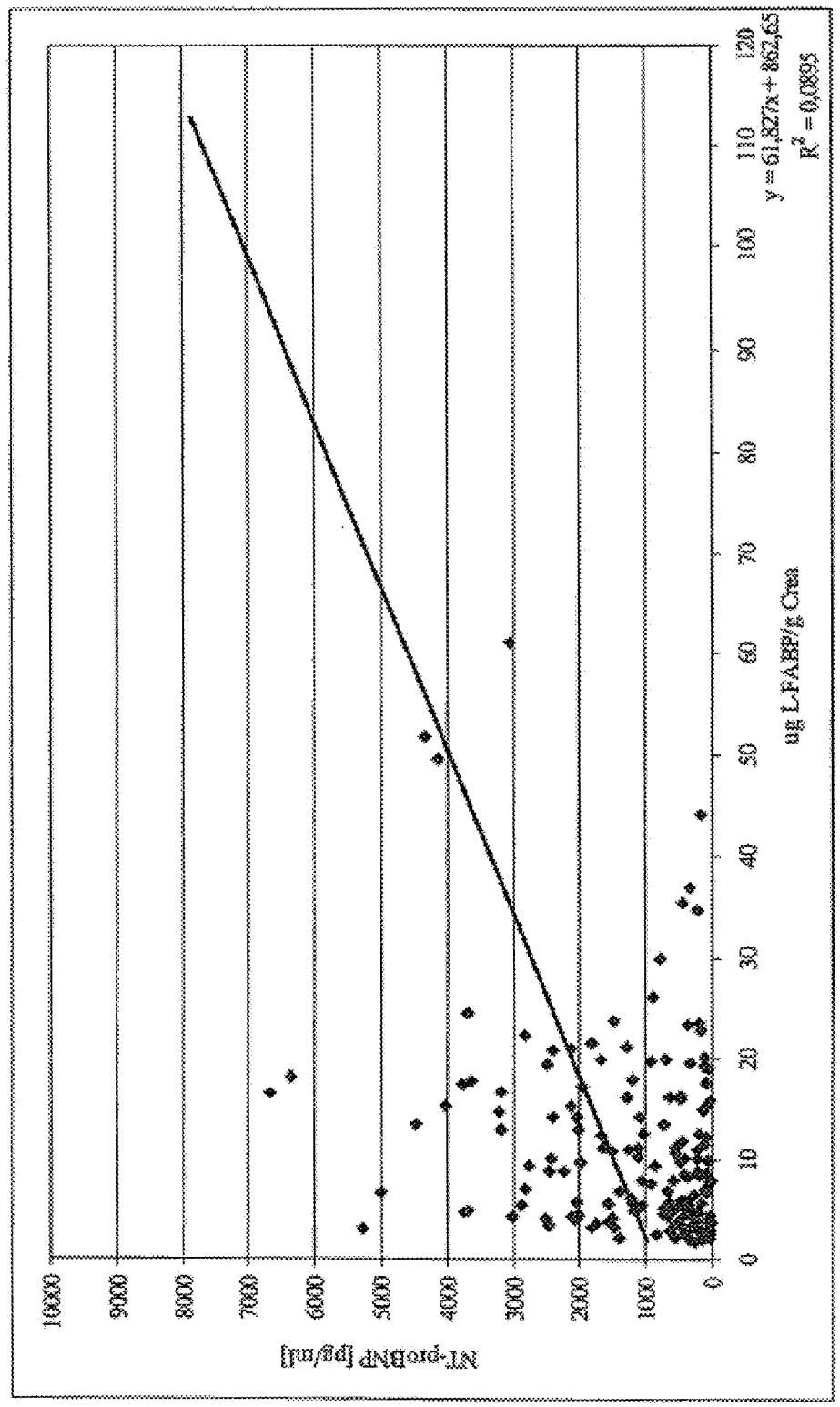
FIG. 3: Correlation of NT-proBNP and L-FABP (L-FABP to creatinine ratio; each dot represents one individual).

The term "identifying" as used herein means assessing whether a subject will be susceptible for a cardiac therapy or not. Particularly, a subject who is susceptible to a cardiac therapy will benefit from the cardiac therapy, preferably, without the risk of adverse side effects on renal function. Thus, the condition of the heart (i.e., the condition with respect to heart function) of the subject will ameliorate (or will at least not worsen) and renal function will not be impaired (or at least will not be significantly impaired). Particularly, the kidney of a subject who is susceptible to a cardiac therapy shall sufficiently exhibit its physiological function when being treated with a cardiac therapy. A subject who is not susceptible to cardiac therapy, preferably, will be at risk of renal failure (particularly, acute renal failure) when taking pharmaceuticals that are (or that may be under certain circumstances) nephrotoxic (for a list of these pharmaceuticals see below, particularly ACE inhibitors). Accordingly, a subject who is not susceptible to a cardiac therapy requires a therapy that does not impair renal function or that impairs renal function only to a low extend. Said therapy shall avoid drugs that may cause acute renal failure.

In summary, a subject who is susceptible from cardiac therapy will, preferably, benefit from the therapy, whereas a subject who is not susceptible will, preferably, not benefit from the therapy. Particularly, a subject who is not susceptible to cardiac therapy will be at risk (i.e., increased risk) of renal failure as a consequence of the therapy.

As will be understood by those skilled in the art, such an assessment (i.e., whether a subject is susceptible to a cardiac therapy or not) is usually not intended to be correct for all (i.e., 100%) of the subjects to be identified. The term, however, requires that a statistically significant portion of subjects can be identified (e.g., a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

The term "subject" as used herein relates to an animal, preferably a mammal, and, more preferably, a human.

However, it is envisaged in accordance with the aforementioned method of the present invention that the subject shall be "in need of a cardiac therapy". Therefore, the subject, preferably, shall have a cardiac dysfunction or disorder. More preferably, the subject shall suffer from heart failure, i.e., exhibit symptoms and/or physical signs known to be associated with heart failure.

The term "heart failure" as used herein relates to an impaired systolic and/or diastolic function of the heart. Preferably, heart failure referred to herein is also chronic heart failure. Heart failure can be classified into a functional classification system according to the New York Heart Association (NYHA). Patients of NYHA Class I have no obvious symptoms of cardiovascular disease but already have objective evidence of functional impairment. Physical activity is not limited, and ordinary physical activity does not cause undue fatigue, palpitation, or dyspnea (shortness of breath). Patients of NYHA class II have slight limitation of physical activity. They are comfortable at rest, but ordinary physical activity results in fatigue, palpitation, or dyspnea. Patients of NYHA class III show a marked limitation of physical activity. They are comfortable at rest, but less than ordinary activity causes fatigue, palpitation, or dyspnea. Patients of NYHA class IV are unable to carry out any physical activity without discomfort. They show symptoms of cardiac insufficiency at rest. Heart failure, i.e., an impaired systolic and/or diastolic function of the heart, can be determined also by, for example, echocardiography, angiography, szintigraphy, or magnetic resonance imaging. This functional impairment can be accompanied by symptoms of heart failure as outlined above (NYHA class II-IV), although some patients may present without significant symptoms (NYHA I). Moreover, heart failure is also apparent by a reduced left ventricular ejection fraction (LVEF). More preferably, heart failure as used herein is accompanied by a left ventricular ejection fraction (LVEF) of less than 60%, of 40% to 60% or of less than 40%.

Preferably, the subject has not experienced an acute coronary syndrome recently. More preferably, the subject has not experienced an acute coronary syndrome within 24 hours, two days, one week, or, most preferably, one month prior to carrying out the method of the present invention (more precisely: prior to obtaining the sample(s) to be analyzed in the context of the method of the present invention). Preferably, the subject has a cardiac troponin level, more preferably a troponin T level, of lower than 0.1 ng/ml (since this would exclude recent acute cardiovascular events).

Said subject, in general, can be an individual with or without an apparent renal disorder. Preferably, the subject does not have an apparent renal disorder. Renal disorders are known to the person skilled in the art. In this context, the term "renal disorder" is considered to relate, preferably, to any disease, injury, or dysfunction of the kidney or affecting the kidney, more particularly affecting the capacity of the kidney for waste removal and/or ultrafiltration. Examples for renal disorders include congenital disorders and acquired disorders. Examples for congenital renal disorders include congenital hydronephrois, congenital obstruction of urinary tract, duplicated ureter, horseshoe kidney, polycystic kidney disease, renal dysplasia, unilateral small kidney. Examples for acquired renal disorders include diabetic or analgesic nephropathy, glomerulonephritis, hydronephrosis (the enlargement of one or both of the kidneys caused by obstruction of the flow of urine), interstitial nephritis, kidney stones, kidney tumors (e.g., Wilms tumor and renal cell carcinoma), lupus nephritis, minimal change disease, nephrotic syndrome (the glomerulus has been damaged so that a large amount of protein in the blood enters the urine. Other frequent features of the nephrotic syndrome include swelling, low serum albumin, and high cholesterol), pyelonephritis, renal failure (e.g., acute renal failure and chronic renal failure). Renal disorders can be diagnosed by any means known and deemed appropriate. Particularly, renal function can be assessed by means of the glomerular filtration rate (GFR). For example, the GFR may be calculated by the Cockgroft-Gault or the MDRD formula (Levey 1999, Annals of Internal Medicine, 461-470). GFR is the volume of fluid filtered from the renal glomerular capillaries into the Bowman's capsule per unit time. Clinically, this is often used to determine renal function. The GFR was originally estimated (the GFR can never be determined, all calculations derived from formulas such as the Cockgroft Gault formula of the MDRD formula deliver only estimates and not the "real" GFR) by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance (CrCl) is therefore a close approximation of the GFR. The GFR is typically recorded in milliliters per minute (mL/min). The normal range of GFR for males is 97 to 137 mL/min, the normal range of GFR for females is 88 to 128 mL/min.

One of the first hints for renal disorder is the presence of protein in urine (micro- or macroalbuminuria) which can be assessed by simple dip stick. The most common blood test used to date is still creatinine while acknowledging its missing accuracy.

Accordingly, a subject without an apparent renal disorder as referred to in the context of the present invention, preferably, has a blood creatinine level of lower than 1.6 mg/dl, more preferably of lower than 1.2 mg/dl, even more preferably, lower than 1.0 mg/dl and most preferably of lower than 0.8 mg/dl.

Accordingly, the subject without an apparent renal disorder as referred to in the context of the present invention, preferably, has a GFR of larger than 45 mL/min, more preferably of larger than 60 mL/min, and most preferably of larger than 90 mL/min.

The term "cardiac therapy" encompasses, preferably, those treatment regimens which comprise the administration of pharmaceuticals suitable for the treatment cardiac dysfunctions and, particularly, for heart failure. Pharmaceuticals suitable for the treatment of heart failure are well known in the art, see e.g., Heart Disease, 2005, $7^{th}$ Edition, Eds. Braunwald, Elsevier Sounders, see tables 23-1, 23-6, 23-7, 23-8, 23-9, 23-10. Preferably, the administration of such pharmaceuticals aims to treat the symptoms and signs of heart failure and which aim to prevent a further progression of heart failure. Also contemplated are pharmaceuticals that aim to treat comorbidities of heart failure such as arterial hypertension, arteriosclerosis, osteoporosis, and osteoarthritis.

However, it is contemplated that the pharmaceuticals, although being suitable for the therapy of heart failure, may impair renal function. Accordingly, the pharmaceuticals for cardiac therapy, preferably, have or (may have under certain circumstances) the adverse side effect of decreasing (impairing) renal function, and, thus, are (or may be under certain circumstances) nephrotoxic. Drugs suitable for the treatment of heart failure (but known to impair renal function), are preferably, ACE (angiotensin converting enzyme)-inhibitors, calcium antagonists (calcium channel blockers), angiotensin-receptor blockers, digoxin, digitoxin, aldosterone antagonists, and diuretics. Most preferably, the term "cardiac therapy" refers to a therapy with ACE-inhibitors.

ACE-inhibitors are known to the person skilled in the art. Although ACE inhibitors are known to be renoprotective (i.e., nephroprotective) in general, they may cause renal failure in a subpopulation of subjects.

Preferred examples for ACE inhibitors include benazepril, captopril, cilazapril, enalapril, fosinopril, lisinopril, moexipril, perindopril, quinapril, ramipril, spirapril, and trandolapril. A particularly preferred ACE-inhibitor is lisinopril.

The term "aldosterone antagonist" relates to a compound being capable of counteracting the effect of aldosterone, e.g., by competitive blockage of aldosterone receptors found in renal tubules. Preferably, the aldosterone antagonist is spironolacton or eplerenone. Pharmaceuticals that aim to treat comorbidities of heart failure are, preferably, non-steroidal anti-rheumatics. Non-steroidal anti-rheumatics (also referred to as non-steroidal anti-inflammatory drugs or NSAIDs) are known to the person skilled in the art. NSAIDs inhibit cyclooxygenases (also known as prostaglandin-H-synthetases). Cyclooxygenases catalyze the reaction from arachidonic acid to prostaglandin H2 (a cyclic endoperoxide), which is the precursor of prostaglandin I2 (also known as prostacycline), thromboxan A2, and other prostaglandins. Prostaglandins play a significant role in pain, fever, and inflammatory reactions. There are two isoforms of cyclooxygenases, Cox-1 and Cox-2. The Cox-2 gene is an immediate early gene and is induced under conditions of tissue damage, pain reactions, or inflammatory reactions. Thus, NSAIDs include, preferably, Cox-1 inhibitors and, more preferably, Cox-2 inhibitors. Preferably, Cox-2 inhibitors are selective Cox-2 inhibitors, and thus compounds which, under therapeutic conditions, do inhibit expression or, preferably, the enzymatic function of Cox-2, whereas not significantly inhibiting expression or, preferably, the enzymatic function of Cox-1. Examples for selective Cox-2 inhibitors include coxibes (e.g., celecoxib, rofecoxib, etoricoxib, valdecoxib, parecoxib (a pro-drug of valdecoxib), lumiracoxib), meclofenatmate, sulindac sulphide, diclofenac, nimesulide, meloxicam, etodolac, NS398, L-745,337, DFP (3-(2-propyloxy)-4-(4-methylsulphonylphenyl)-5,5-dimethylfuranone). The latter three compounds are described in Warner, T. D., et al., 1999. Examples for unspecific NSAIDs include Ibuprofen; Flurbiprofen; Naproxen; Flufenamic Acid; Mefenamic Acid; Piroxicam; Diclofenac; Phenbutazone Sodium Glycerate; Indometacin; Tenoxicam.

The term "liver-type fatty acid binding protein" (L-FABP, frequently also referred to as FABP1 herein also referred to as liver fatty acid binding protein) relates to a polypeptide being a liver type fatty acid binding protein and to a variant thereof. Liver-type fatty acid binding protein is an intracellular carrier protein of free fatty acids that is expressed in the proximal tubules of the human kidney. Kamijo et al. (Urinary liver-type fatty acid binding protein as a useful biomarker in chronic kidney disease. Mol. Cell Biochem. 2006; 284) reported that urinary excretion of L-FABP may reflect various kind of stresses that cause tubulointerstitial damage and may be a useful clinical marker of the progression of chronic renal disease. For a sequence of human L-FABP, see e.g., Chan et al.: Human liver fatty acid binding protein eDNA and amino acid sequence. Functional and evolutionary implications J. Biol. Chem. 260 (5), 2629-2632 (1985) or GenBank Acc. Number M10617.1.

The term "L-FABP" encompasses also variants of L-FABP, preferably, of human L-FABP. Such variants have at least the same essential biological and immunological properties as L-FABP. In particular, they share the same essential biological and immunological properties if they are detectable by the same specific assays referred to in this specification, e.g., by ELISA Assays using polyclonal or monoclonal antibodies specifically recognizing the L-FABP. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the L-FABP. How to determine the degree of identity is specified elsewhere herein. Variants may be allelic variants or any other species specific homologs, paralogs, or orthologs. Moreover, the variants referred to herein include fragments of L-FABP or the aforementioned types of variants as long as these fragments have the essential immunological and biological properties as referred to above. Such fragments may be, e.g., degradation products of the L-FABP. Further included are variants which differ due to posttranslational modifications such as phosphorylation or myristylation. The term "L-FABP", preferably, does not include heart FABP, brain FABP and intestine FABP.

The method of the present invention comprises determining at least one further polypeptide from the group of a cardiac troponin and a natriuretic peptide. Preferably, the at least one further polypeptide is a cardiac troponin. More preferably, the at least one further polypeptide is a natriuretic peptide. Most preferably, both a natriuretic peptide and a cardiac troponin are determined in the context of the method of the present invention. Compared to the determination of a natriuretic peptide or a cardiac troponin alone, the determination of both of a natriuretic peptide and a cardiac troponin allows that a statistically more significant portion of subjects can be correctly identified. Thus, the determination of both markers markedly enhances diagnostic and prognostic value. However, the determination of a single marker (a cardiac troponin or a natriuretic peptide) already allows that a statistically significant portion of subjects can be correctly identified.

The term "natriuretic peptide" comprises atrial natriuretic peptide (ANP)-type and brain natriuretic peptide (BNP)-type peptides and variants thereof having the same predictive potential. Natriuretic peptides according to the present invention comprise ANP-type and BNP-type peptides and variants thereof (see e.g., Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Preferably, natriuretic peptides according to the present invention are NT-proANP, ANP, and, more preferably, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NT-proBNP is 120 min longer than that of BNP, which is 20 min (Smith 2000, J Endocrinol. 167: 239-46.). Preanalytics are more robust with NT-proBNP allowing easy transportation of the sample to a central laboratory (Mueller 2004, Clin Chem Lab Med 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller loc. cit.; Wu 2004, Clin Chem 50: 867-73.). Therefore, depending on the time-course or properties of interest, either measurement of the active or the inactive forms of the natriuretic peptide can be advantageous. The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of the specific sequence for human NT-proBNP discussed above. Specifically, envisaged are variant polypeptides which are on the amino acid level preferably, at least 50%, 60%, 70%, 80%, 85%, 90%, 92%, 95%, 97%, 98%, or 99% identical, to human NT-proBNP. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wisc.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are immunological and/or biological properties. Preferably, the NT-proBNP variants have immunological properties (i.e., epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Invest 230:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac troponin refers to troponin T and/or troponin I, and, most preferably, to troponin T. It is to be understood that isoforms of Troponins may be determined in the method of the present invention together, i.e., simultaneously or sequentially, or individually, i.e., without determining the other isoform at all. Amino acid sequences for human troponin T and human troponin I are disclosed in Anderson, loc cit and Ferrieres 1998, Clinical Chemistry, 44: 487-493.

The term "cardiac troponin" encompasses also variants of the aforementioned specific Troponins, i.e., preferably, of troponin I, and more preferably, of troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the cardiac Troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. Such fragments may be, e.g., degradation products of the Troponins. Further included are variants which differ due to posttranslational modifications such as phosphorylation or myristylation.

Determining the amount of a natriuretic peptide, a cardiac troponin, or liver type fatty acid binding protein, or any other peptide or polypeptide referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e., a component not being the peptide or polypeptide itself) or a biological read out system, e.g., measurable cellular responses, ligands, labels, or enzymatic reaction products. Preferably, the amount of a cardiac troponin, particularly troponin T, is determined with a very sensitive troponin T test system in order to allow a reliable determination of very low cardiac troponin amounts, preferably the test system is capable of determining amounts of 0.001 ng/ml of a cardiac troponin. A particularly preferred troponin T assay in the context of the present invention is the Elecsys® 2010 analyzer (Roche Diagnostics) with a detection limit of from 0.001 ng/ml to 0.0015 ng/ml.

The term "sample" refers to a sample of a body fluid, to a sample of separated cells or to a sample from a tissue or an organ. Samples of body fluids can be obtained by well known techniques and include, preferably, samples of blood, plasma, serum, urine, samples of blood, plasma or serum. It is to be understood that the sample depends on the marker to be determined. Therefore, it is encompassed that the polypeptides as referred to herein are determined in different samples. L-FABP, preferably, is determined in a urine sample. Cardiac troponins and natriuretic peptides are, preferably, determined in a blood serum or blood plasma sample.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g., reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Preferably, determining the amount of a peptide or polypeptide comprises the steps of (a) contacting a cell capable of eliciting a cellular response the intensity of which is indicative of the amount of the peptide or polypeptide with the peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab and $F(ab)_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g., according to its size on a Western Blot, or by its relatively higher abundance in the sample. Binding of the ligand can be measured by any method known in the art. Preferably, the method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g., magnetic beads", including paramagnetic and superparamagnetic labels), and fluorescent labels. Enzymatically active labels include e.g., horseradish peroxidase, alkaline phosphatase, beta-Galactosidase, Luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemiluminescence, which can be measured according to methods known in the art (e.g., using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Further fluorescent labels are available e.g., from Molecular Probes (Oregon). Also the use of quantum dots as fluorescent labels is contemplated. Typical radioactive labels include $^{35}S$, $^{125}I$, $^{32}P$, $^{33}P$ and the like. A radioactive label can be detected by any method known and appropriate, e.g., a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labelling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing the ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g., a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the polypeptide or peptide as well as any value or parameter which correlates thereto or can be derived therefrom. Such values or parameters comprise intensity signal values from all specific physical or chemical properties obtained from the peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e., automatically provide the desired assessment in a suitable output format. Based on the comparison of the amount determined in step a) and the reference amount, it is possible to assess whether a subject is susceptible for a cardiac therapy and, thus, belongs to the group of subjects which can be successfully treated by the cardiac therapy. Therefore, the reference amount is to be chosen so that either a difference or a similarity in the compared amounts allows identifying those the test subject which belong into the group of subjects susceptible for cardiac therapy or identifying those test subjects which are not susceptible for a cardiac therapy.

Accordingly, the term "reference amount" as used herein refers to an amount which allows assessing whether a subject in need thereof will be susceptible for a cardiac therapy as referred to above. Accordingly, the reference may either be derived from (i) a subject known to have been successfully treated, i.e., a subject who did benefit from the cardiac therapy, preferably, without the occurrence of adverse effects on renal function such as renal failure (preferably acute renal failure), or (ii) a subject known to have been not successfully treated, i.e., a subject whose renal function was decreased due to the therapy, particularly a subject who developed renal failure (preferably acute renal failure) due to the therapy and, thus, did not derive benefits from the treatment regimen. Moreover, the reference amounts for the various biomarkers, thus L-FABP and at least one further polypeptide selected from the natriuretic peptide and a cardiac troponin may define a threshold amount, whereby (i) an amount of the of at least one further polypeptide (preferably of both a cardiac troponin and a natriuretic peptide) larger than the corresponding threshold(s) and an amount of L-FABP lower than the threshold for L-FABP shall be indicative for a subject being susceptible for a cardiac therapy while (i) an amount of the of at least one further polypeptide (preferably of both a cardiac troponin and a natriuretic peptide) lower than the corresponding threshold(s) and an amount of L-FABP larger than the threshold for L-FABP shall be an indicator for a subject which is not susceptible to the therapy, and, thus requires a therapy that has lower adverse side effects on renal function or that does not have adverse side effect on renal function at all. The reference amount applicable for an individual subject may vary depending on various physiological parameters such as age, gender, or subpopulation, as well as on the means used for the determination of the polypeptides or peptides referred to herein. A suitable reference amount may be determined by the method of the present invention from a reference sample to be analyzed together, i.e., simultaneously or subsequently, with the test sample. A preferred reference amount serving as a threshold may be derived from the upper limit of normal (ULN), i.e., the upper limit of the physiological amount to be found in a population of apparently healthy subjects. The ULN for a given population of subjects can be determined by various well known techniques. A suitable technique may be to determine the median of the population for the peptide or polypeptide amounts to be determined in the method of the present invention.

The reference amount defining a threshold amount for L-FABP as referred to in accordance with the present invention is, preferably, 6 ng/ml, more preferably, 10 ng/ml and, most preferably, 8 ng/ml. If the amount of L-FABP is related to the amount of urinary creatinine (ratio of urinary L-FABP to urinary creatinine: L-FABP/creatinine), then the reference defining a threshold, preferably, is a urinary L-FABP/creatinine ratio of 12 µg L-FABP/g creatinine, more preferably, a ratio of 20 µg/g and, most preferably, a ratio of 16 µg/g.

A reference amount defining a threshold amount for a natriuretic peptide and, in particular, for NT-proBNP, as referred to in accordance with the present invention is, preferably, 600 pg/ml, more preferably, 400 pg/ml and, most preferably, 200 pg/ml.

A reference amount defining a threshold amount for a cardiac troponin and, in particular, for troponin T as referred to in accordance with the present invention is, preferably, 10 pg/ml, and, more preferably, 4 pg/ml and, most preferably, 6 pg/ml.

An amount of (i) L-FABP lower than the reference amount (or, respectively, a L-FABP to creatinine ratio lower than the reference ratio, L-FABP to creatinine), and (ii) and an amount of the at least one further polypeptide of the group of a natriuretic peptide and a cardiac troponin larger than the reference amount is, preferably, indicative for a subject being susceptible to a cardiac therapy. More preferably, an amount of (i) L-FABP lower than the reference amount (or, respectively, a L-FABP to creatinine ratio lower than the reference ratio), and an amount of a natriuretic peptide and a cardiac troponin larger than the reference amounts for a natriuretic peptide and a cardiac troponin is, preferably, indicative for a subject being susceptible to a cardiac therapy.

An amount of (i) L-FABP larger than the reference amount (or, respectively, a L-FABP to creatinine ratio larger than the reference ratio), and (ii) and an amount of the at least one further polypeptide of the group of a natriuretic peptide and a cardiac troponin lower than the reference amounts for a natriuretic peptide (in particular NT-proBNP) and a cardiac troponin (in particular troponin T) is, preferably, indicative for a subject not being susceptible to a cardiac therapy. More preferably, an amount of (i) L-FABP larger than the reference amount (or, respectively, a L-FABP to creatinine ratio larger than the reference ratio), and an amount of (ii) a natriuretic peptide and a cardiac troponin lower than the reference amounts for a natriuretic peptide and a cardiac troponin, respectively, is indicative for a subject not being susceptible to a cardiac therapy. Said subject, preferably, only suffers from a mild heart failure (particularly, the patient may belong to NYHA Class I or Class II) that, preferably, does not require an intensive pharmaceutical therapy with drugs as referred to in the context of cardiac therapy. However, the subject shows an impaired renal function as indicated by the amount of L-FABP indicating the subject only shall take pharmaceuticals without adverse side effects on renal function (or with low adverse side effects on renal function) Preferably, the subject is treated with beta adrenergic blockers. Also contemplated is a medication with low dosages of ACE inhibitors. Said low dosages will be beneficial to his cardiac condition and will impair renal function only to a low extend (see also comments in the next paragraph). Moreover, by the described therapy health care cost will be reduced.

In the case that the amounts of L-FABP and the at least one further polypeptide from the group of cardiac Troponins and a natriuretic peptide are larger than the reference amounts, the subject needs to be carefully monitored with respect to his renal and cardiac condition. Said subject requires a therapy that does not impair renal function or that impairs renal function only to a low extend. Said subject shall take pharmaceuticals against heart failure, however, the pharmaceuticals to be taken need to be carefully adjusted considering both the insufficient renal and cardiac condition of the subject. Preferably, pharmaceuticals shall be chosen that are known to have low or no adverse side effects on renal function and, thus with low or without nephrotoxicity (and thus with low or without any impairment on renal function) such as β-adrenergic blockers. Also contemplated are, preferably, mild diuretics. Moreover, in order to limit adverse side effects on renal function, the dosage of pharmaceuticals which impair renal function can be reduced. In general, the higher the amount of L-FABP, the lower shall be the dosage of the respective pharmaceutical to be administered. It is particular contemplated to reduce the dosage of ACE (angiotensin converting enzyme)-inhibitors (particularly of ACE inhibitors that are or may be under certain circumstances nephrotoxic), angiotensin-receptor blockers and non-steroidal anti-rheumatics. The dosage of the pharmaceuticals may be slowly increased. However, when increasing the dosage, it is required to monitor the effect of the increased dosage carefully. Moreover, a subject not being susceptible to a cardiac therapy, preferably, shall take pharmaceuticals suitable for ameliorating renal function such as Mesna (Uromitexan®). Preferably, a subject not being susceptible to the administration of the pharmaceuticals, preferably, shall take pharmaceuticals suitable for the treatment of heart failure but without any or with low adverse side effects on renal function. Also contemplated is that the subject is susceptible to the administration of reduced dosages of pharmaceuticals that suitable for the therapy of heart failure but that have adverse side effects on renal function in order to decrease the risk of further renal damage. Taken together, patients with increased U-L-FABP are required to be carefully monitored with respect to their renal function, particularly when increasing the dosage of nephrotoxic pharmaceuticals, in particular ACE inhibitors.

In the case that the amounts of L-FABP and the at least one further polypeptide from the group of cardiac Troponins and a natriuretic peptide are lower than the reference amounts, the subject is susceptible to any form of cardiac therapy as referred to herein. Since the subject, although suffering from heart failure, has a relatively good cardiac condition, the subject does not require an intensive treatment with pharmaceuticals.

Advantageously, it was found in the studies underlying the present invention that the determination of L-FABP, and at least one further polypeptide from the group of a cardiac troponin and a natriuretic peptide is suitable for identifying a subject being susceptible for a cardiac therapy. The aforementioned marker combination, allows both assessing cardiac and renal function. Accordingly, the combination allows choosing a pharmaceutical therapy which aims to achieve a more favourable balance between the benefits of an individual treatment regimen and the adverse effects. The method of the present invention is more reliable than prior art since it was shown that L-FABP and at least one further polypeptide from the group of a cardiac troponin and a natriuretic peptide are required to reliably make decisions on the treatment of patients suffering from heart failure. As it can be seen on FIG. 1, the determination of L-FABP allows a more reliable identification of subjects with impaired renal function than creatinine. By additionally determining a cardiac marker in a sample of a subject, the cardiac condition can be assessed. Particularly, the method of the present invention allows to identify subjects susceptible to the administration of nephrotoxic pharmaceuticals, i.e., pharmaceuticals that may impair renal function as referred to herein and to decide on the use and/or the dosage of pharmaceuticals, particularly ACE inhibitors.

The method of the present invention is advantageous since it allows for identifying those patients which do not have an apparent renal disease, which are, however, at risk of suffering from renal failure as a consequence of the intake of specific drugs referred to elsewhere herein. Although these drugs may have renoprotive effects for the majority of patients, there is a subpopulation of patients who will not benefit from the drugs. By carrying out the method of the present invention, patients belonging to this subgroup can be reliably identified.

The present invention, preferably, also relates to a method on deciding on a treatment of a subject as referred to above based on the aforementioned steps (thus, determining the amounts of L-FABP, and at least one further polypeptide from the group of a cardiac troponin and a natriuretic peptide in a sample and comparing the amounts to reference amounts). Therefore, the method of the present invention allows to decide which pharmaceuticals should be taken by the subject, e.g., to focus more on the treatment of heart failure or to focus more on preventing further impairment of renal function.

In a preferred embodiment of the method of the present invention it is determined whether a subject who already gets cardiac therapy (and, thus is being treated with pharmaceuticals for cardiac therapy as referred to above, in particular nephrotoxic ACE inhibitors), is susceptible to cardiac therapy, comprising the steps of a) determining the amounts of liver fatty acid binding protein (L-FABP), and of at least one further polypeptide from the group of a cardiac troponin and a natriuretic peptide, in at least one sample of a subject who suffers from heart failure and is in need of a cardiac therapy, b) comparing the amounts of the liver fatty acid binding protein, and at least one further polypeptide from the group of a cardiac troponin and a natriuretic peptide, as determined in step a) to suitable reference amounts, and c) identifying a subject being susceptible to a cardiac therapy.

The aforementioned method, particularly allows monitoring subjects which suffer from heart failure and are being treated with pharmaceuticals that impair renal function. If renal function worsens, other pharmaceuticals or a lower dosage of the administered pharmaceutical shall be considered.

Moreover, the present invention relates to a device for identifying a subject being susceptible to a cardiac therapy adapted to carry out the method of the present invention comprising means for determining the amounts of liver fatty acid binding protein, and of least one further polypeptide from the group of a cardiac troponin and a natriuretic peptide in a sample of the subject who suffers from heart failure, and means for comparing the amounts to suitable reference amounts, whereby a subject being susceptible to cardiac therapy is identified.

The term "device" as used herein relates to a system of means comprising at least the aforementioned means operatively linked to each other as to allow the prediction. Preferred means for determining the amount of L-FABP, and of at least one further polypeptide from the group of a cardiac troponin and natriuretic peptides, and means for carrying out the comparison are disclosed above in connection with the method of the invention. Preferably, the device comprises both means for determining the amounts of a natriuretic peptide and means for determining the amounts of a cardiac troponin. How to link the means in an operating manner will depend on the type of means included into the device. For example, where means for automatically determining the amount of the peptides are applied, the data obtained by the automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test strips are used for determining the amount of the peptides or polypeptides, the means for comparison may comprise control strips or tables allocating the determined amount to a reference amount. The test strips are, preferably, coupled to a ligand which specifically binds to the peptides or polypeptides referred to herein. The strip or device, preferably, comprises means for detection of the binding of the peptides or polypeptides to the ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of raw data which need interpretation by the clinician. Preferably, the output of the device is, however, processed, i.e., evaluated, raw data the interpretation of which does not require a clinician. Further preferred devices comprise the analyzing units/devices (e.g., biosensors, arrays, solid supports coupled to ligands specifically recognizing the polypeptide, plasmon surface resonance devices, NMR spectrometers, mass-spectrometers etc.) or evaluation units/devices referred to above in accordance with the method of the invention.

Further encompassed by the present invention is a kit for carrying out the method of the present invention comprising means for determining the amount of liver fatty acid binding protein, and of at least one further polypeptide from the group of a cardiac troponin and a natriuretic peptide in a sample of a subject suffering from heart failure and means for comparing the amounts to reference amounts, whereby a subject being susceptible to a cardiac therapy is identified.

The term "kit" as used herein refers to a collection of the aforementioned means, preferably, provided separately or within a single container. The components of the kit may be comprised by separate vials (i.e., as a kit of separate parts) or provided in a single vial. Moreover, it is to be understood that the kit of the present invention is to be used for practising the methods referred to herein above. It is, preferably, envisaged that all components are provided in a ready-to-use manner for practising the methods referred to above. Further, the kit preferably contains instructions for carrying out the methods. The instructions can be provided by a user's manual in paper- or electronic form. For example, the manual may comprise instructions for interpreting the results obtained when carrying out the aforementioned methods using the kit of the present invention.

Preferably, the kit comprises both means for determining the amounts of a natriuretic peptide and means for determining the amounts of a cardiac troponin and means for comparing the amounts to reference amounts.

Furthermore, the present invention relates to the use of liver fatty acid binding protein, and of at least one further polypeptide from the group of a cardiac troponin and a natriuretic peptide, or of means for determining the amount of liver fatty acid binding protein, and of at least one further polypeptide from the group of a cardiac troponin and a natriuretic peptide for the manufacture of a diagnostic composition for identifying a subject being susceptible to a cardiac therapy.

The definitions and explanations given above apply mutatis mutandis to the following.

Furthermore, the present invention also relates to a method for identifying a subject being susceptible to the administration of a contrast medium comprising the steps of
- a) determining the amounts of liver fatty acid binding protein, and of at least one further polypeptide from the group of a cardiac troponin and a natriuretic peptide in a sample of a subject,
- b) comparing the amounts of liver fatty acid binding protein (L-FABP) and the at least one further polypeptide determined in step a) to suitable reference amounts, and
- c) identifying a subject being susceptible to the administration of a contrast medium.

The term "contrast medium" is known by the skilled person. The term, preferably, relates to any substance that is deemed appropriate, when administered to a subject, to increase the contrast, preferably, in X-ray imaging by affecting the attenuation of X-rays, and, therefore, to enhance the visibility of structures and fluids. Preferably, a contrast medium is a non-iodine based contrast medium and more preferably, an iodine based contrast medium.

Preferably, the administration of a contrast medium, particularly, of an iodine based contrast medium, is for computed tomography, and, even more preferably, for angiography, and most preferably, for coronary angiography. Further contemplated by the present invention is the administration of a suitable contrast medium for ultrasonic examination or magnetic resonance imaging (MRI).

Preferably, the amounts of the biomarkers as referred to above are determined in at least one sample that are obtained prior to the intended administration of a contrast medium, more preferably, at least one hour, at least eight hours, and, most preferably, at least 24 prior to the intended administration.

All references cited in this specification are herewith incorporated by reference with respect to their entire disclosure content and the disclosure content specifically mentioned in this specification.

The following examples shall merely illustrate the invention. They shall not be construed, whatsoever, to limit the scope of the invention.

Example 1

The amounts of serum NT-proBNP, serum troponin T, urinary L-FABP and creatinine were determined in 165 patients with heart failure. Moreover, the biomarkers were determined in healthy individuals (FIG. 1). In subjects with heart failure, U-L-FABP as a marker for tubular damage did not correlate stringently with creatinine, a marker for the renal excretion rate. Also, U-L-FABP did not correlate stringently with NT-proBNP and troponin T. Of the patients analyzed, 41 had an U-L-FABP to Creatinine ratio lower than 5.6 µg (5.6 µg/g: $75^{th}$ percentile of a population with healthy subjects), and 124 had an U-L-FABP to creatinine ratio larger than 5.6 µg/g. Patients with increased U-L-FABP are required to be carefully monitored with respect to their renal function.

The measurement of (i) U-L-FABP, and (ii) troponin T and/or NT-proBNP allows assessing both tubular damage and cardiac function. Based on the measurements, decisions on the administration of pharmaceuticals for the treatment of heart failure and on the dosage of these pharmaceuticals can be made in order to achieve a more favourable balance between the benefits and the adverse side effects of pharmaceuticals that may impair renal function.

Example 2

A 62 years old patient with known coronary artery disease and established heart failure a serum NT-proBNP level of 195 pg/ml and a serum troponin T level of 5 pg/ml. The patient has a daily intake of the ACE-inhibitor Lisinopril of 20 mg. The daily intake, however, shall be increased to 40 mg. The plasma creatinine level (1.1 mg/dl) as well as the creatinine clearance (75 ml/min) are determined indicating that that the patient does not have an apparent renal disorder. The urine L-FABP level is determined (10.5 µg/g creatinine). Four weeks after increasing the daily intake of Lisinopril, the aforementioned parameters are determined again (creatinine 1.8 mg/dl; U-L-FABP/creatinine 12 µg/g. Since there is a risk of acute renal failure, the daily intake of Lisinopril is reduced to 20 mg and an AT blocker is administered.

Example 3

A 64 years old female patient with known coronary artery disease (systolic dysfunction, NT-proBNP 800 pg/ml, troponin T 12 pg/ml, plasma creatinine 1.1 mg/dl) presents at her cardiologist. The patient has already a daily intake of Lisinopril of 20 mg. Due to the increased level levels of NT-proBNP and TroponinT, the daily intake of the Lisinopril shall be increased to 40 or even 60 mg. The U-L-FABP level is determined (7 µg/g creatinine). Six weeks after increasing the daily intake to 40 mg, the creatinine level as well as the U-L-FABP level remain nearly unchanged (creatinine 1.1 mg/dl; U-L-FABP 6 µg/g creatinine). In the following the daily intake is increased to 60 mg. Even the second dose increase does not significantly alter the creatinine and U-L-FABP levels. The NT-proBNP and troponin T levels, however, are decreased as compared to the first examination (NT-proBNP 720 pg/ml, troponin T 9 pg/ml). Thus, the patient benefits from the therapy.

What is claimed is:

1. A method for identifying a subject that benefits from a cardiac therapy without a risk of renal failure, wherein the subject is suffering from heart failure and is without an apparent renal disorder as assessed by glomerular filtration rate or creatinine clearance, the method comprising the steps of
   - a) contacting a sample from the subject with a ligand having specific binding affinity for liver fatty acid binding protein (L-FABP),
   - b) contacting a sample from the subject with a ligand having specific binding affinity for an additional polypeptide from the group consisting of a cardiac troponin and a natriuretic peptide;
   - c) calculating an amount of L-FABP based on the contacting step (a);
   - d) calculating an amount of additional polypeptide based on contacting step (c);
   - e) comparing the calculated amount of the L-FABP to a reference amount of L-FABP;
   - f) comparing the calculated amount of additional polypeptide to a reference amount of additional polypeptide, and g) identifying the subject as one who will benefit from cardiac therapy without a risk of renal failure only when the calculated amount of L-FABP is lower than the reference amount of L-FABP and when the calculated amount of the additional polypeptide is greater than the reference amount of additional polypeptide.

2. The method of claim 1, wherein the reference amount for L-FABP is 8 ng/ml, and wherein the cardiac troponin is troponin T and the reference amount for troponin T is 6 pg/ml, and wherein the natriuretic peptide is NT-proBNP and the reference amount for NT-proBNP is 200 pg/ml.

3. The method of claim 1, wherein the cardiac therapy is administration of a pharmaceutical for treatment of heart failure.

4. The method of claim 3, wherein the pharmaceutical is an angiotensin-converting enzyme (ACE) inhibitor.

5. The method of claim 1 wherein the cardiac troponin is troponin T and the natriuretic peptide is NT-proBNP.

6. The method of claim 1, wherein the sample contacted in step (a) is a urine sample and sample contacted in step (b) is a blood, blood serum, or plasma sample.

7. A method for identifying a subject that benefits from a cardiac therapy without a risk of renal failure, wherein the subject is suffering from heart failure and is without an apparent renal disorder as assessed by glomerular filtration rate or creatinine clearance, the method comprising the steps of;

contacting a sample from the subject with a specific binding ligand for liver fatty acid binding protein (L-FABP);

contacting a sample from the subject with a specific binding ligand for a cardiac troponin; contacting a sample from the subject with specific binding ligand for a natriuretic peptide calculating an amount of L-FABP, an amount of cardiac troponin and an amount of natriuretic peptide based on the respective contacting steps;

comparing the calculated amount of the L-FABP to a reference amount of L-FABP;

comparing the calculated amount of the cardiac troponin to a reference amount of cardiac troponin;

comparing the calculated amount of the natriuretic peptide to a reference amount of natriuretic peptide; and identifying the subject as one who will benefit from cardiac therapy without a risk of renal failure only when the calculated amount of L-FABP is lower than the reference amount of L-FABP, when the calculated amount of cardiac troponin is greater than the reference amount of cardiac troponin, and when the calculated amount of natriuretic peptide is greater than the reference amount of natriuretic peptide.

8. The method of claim 7, wherein the reference amount of L-FABP is 8 ng/ml, and wherein the cardiac troponin is troponin T and the reference amount for troponin T is 6 pg/ml, and wherein the natriuretic peptide is NT-proBNP and the reference amount for NT-proBNP is 200 pg/ml.

9. The method of claim 1, wherein the renal failure is acute renal failure.

10. The method of claim 7, wherein the renal failure is acute renal failure.

* * * * *